United States Patent [19]

Lafon

[11] Patent Number: 4,933,370

[45] Date of Patent: Jun. 12, 1990

[54] 1-AMINOPHENYL-2-DIMETHYLAMINO-PROPANONE DERIVATIVES, METHOD OF PREPARATION AND USE IN THERAPY

[75] Inventor: Louis Lafon, Paris, France

[73] Assignee: Laboratoire L. Lafon, Maisons Alfort, France

[21] Appl. No.: 304,257

[22] Filed: Jan. 31, 1989

[30] Foreign Application Priority Data

Feb. 10, 1988 [FR] France .............................. 88 01564

[51] Int. Cl.$^5$ .......................................... A61K 31/165
[52] U.S. Cl. .................................... 514/630; 514/649; 564/220; 564/345
[58] Field of Search ................. 564/345, 220; 514/649, 514/630

[56] References Cited

U.S. PATENT DOCUMENTS

| | | | |
|---|---|---|---|
| 3,536,712 | 10/1970 | Keck et al. | 564/363 |
| 4,355,045 | 10/1982 | Preston et al. | 564/220 |
| 4,461,914 | 7/1984 | Bentley | 564/357 |

FOREIGN PATENT DOCUMENTS

| | | | |
|---|---|---|---|
| 0138714 | 10/1984 | European Pat. Off. | 564/220 |
| 0174242 | 8/1985 | European Pat. Off. | 564/345 |
| 1943777 | 9/1970 | Fed. Rep. of Germany | 564/345 |

OTHER PUBLICATIONS

Fieser et al, "Reagents for Organic Synthesis", p. 139 (1972).

Primary Examiner—James H. Reamer
Attorney, Agent, or Firm—Wegner & Bretschneider

[57] ABSTRACT

The present invention relates, by way of novel industrial products, to 1-(4-aminophenyl)-2-dimethylaminopropanone derivatives which are selected from:
(a) the compounds having the general formula

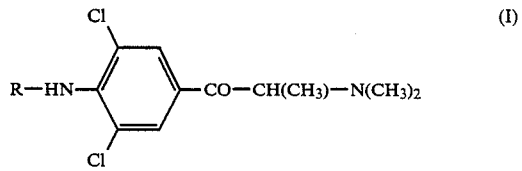

in which R is H or $CH_3CO$, and
(b) addition salts thereof.

These products are useful as antidepressants. Furthermore, 1-(4-acetylamino-3,5-dichlorophenyl)-2-dimethylaminopropanone and non-toxic addition salts thereof are useful as immunostimulants.

3 Claims, No Drawings

1-AMINOPHENYL-2-DIMETHYLAMINOPROPANONE DERIVATIVES, METHOD OF PREPARATION AND USE IN THERAPY

FIELD OF THE INVENTION

The present invention relates, by way of novel industrial products, to 1-aminophenyl-2-dimethylaminopropanone derivatives. It further relates to the method for the preparation of these products and to their use in therapy.

PRIOR ART

It is known that 1-aminophenyl-2-aminopropanone derivatives of the formula

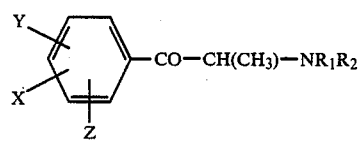

in which:
X is $NH_2$ or $CH_3CONH$,
Y is a hydrogen or halogen atom,
Z is a hydrogen or halogen atom,
$R_1$ is a $C_1$–$C_4$ alkyl group or a $C_3$–$C_6$ cycloalkyl group, and
$R_2$ is the hydrogen atom or a $C_1$–$C_4$ alkyl group, or $R_1$ and $R_2$, taken together, can form, with the nitrogen atom to which they are bonded, a 5-membered to 7-membered N-heterocyclic group which can contain a second heteroatom selected from N, O and S and can be substituted, the said heterocyclic group $NR_1R_2$ being selected from the group consisting of the pyrrolidino, morpholino, thiomorpholino, piperidino, hexamethyleneimino, piperazino, 4-methylpiperazino, 4-(2-hydroxyethyl)piperazino, 4-phenylpiperazino and 4-(p-chlorophenyl)piperazino groups, and addition salts thereof, have already been recommended in the past as antidepressants for the central nervous system (CNS). It is also known that, among the compounds of formula $I_o$ above, only a few products also have beneficial cardiovascular and/or immunological properties, cf. European Pat. No. EP-B-0 174 242 relating to the amino compounds ($X=NH_2$) and European Pat. No. EP-B-0 138 714 relating to the acetylamino compounds ($X=CH_3CONH$).

AIM AND SUBJECT OF THE INVENTION

According to the invention, novel products belonging to the family of the 1-aminophenyl-2-aminopropanone derivatives are proposed and their method of preparation is provided, these novel products being particularly useful in therapy.

These novel products, which are included in the general definitions of formula $I_o$ but which have not yet been specifically described, possess antidepressant properties in the same way as the compounds of formula $I_o$ described in European Pat. Nos. EP-B-0 174 242 and EP-B-0 138 714 mentioned above. They differ from these compounds described in the prior art by the fact that they exert sedative effects whereas the compounds described in European Pat. Nos. EP-B-0 174 242 and B-0 138 714 generally have psychostimulant and/or EP-arousing effects.

According to another aspect of the invention, compounds are proposed which possess beneficial immunological properties whereas their structurally similar homologs are devoid of the said immunological properties, the said compounds being 1-(4-acetylamino-3,5-dichlorophenyl)-2-dimethylaminopropanone and addition salts thereof.

The compounds according to the invention are selected from the group consisting of the compounds having the general formula

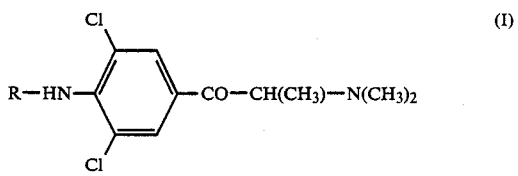

in which R is H or $CH_3CO$, and addition salts thereof.

DETAILED DESCRIPTION OF THE INVENTION

The invention therefore relates to 1-(4-amino-3,5-dichlorophenyl)-2-dimethylaminopropanone, 1-(4-acetylamino-3,5-dichlorophenyl)-2-dimethylaminopropanone and addition salts thereof.

Addition salts are understood here as meaning on the one hand the acid addition salts obtained by reacting a free base of formula I with a mineral or organic acid, and on the other hand the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the free base of formula I. $ICH_3$ and $ClCH_3$ may be mentioned in particular among the compounds which make it possible to obtain ammonium salts. In general, the acid addition salts, such as the hydrochlorides in particular, are preferred to the ammonium salts.

A number of compounds according to the invention have been collated in Table I below without in any way implying a limitation, and they are compared with the two homologs CP-1 and CP-2 described in the above-mentioned documents.

TABLE I

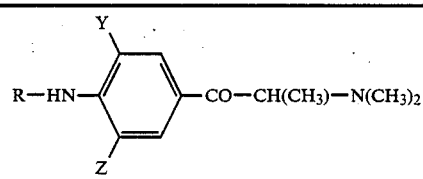

| Example | Code no. | R | Y | Z |
|---|---|---|---|---|
| Ex. 1 (a) | CRL 41 403 | $CH_3CO$ | 3-Cl | 5-Cl |
| Ex. 2 (a) | CRL 41 402 | H | 3-Cl | 5-Cl |
| Ex. 3 (b) | — | $CH_3CO$ | 3-Cl | 5-Cl |
| CP-1 (c,d) | CRL 41 233 | H | H | H |
| CP-2 (a,e) | CRL 41 232 | $CH_3CO$ | H | H |

Notes
(a) monohydrochloride;
(b) methanesulfonate;
(c) dihydrochloride;
(d) described in Example 9 of European patent EP- B-0 174 242;
(e) described in Example 9 of European patent EP- B-0 138 714.

The compounds of formula I can be prepared in accordance with a method known per se by the application of classical reaction mechanisms.

In particular, they can be synthesized by the methods of operation described in European Pat. Nos. EP-B-0 174 242 and EP-B-0 138 714 mentioned above.

The method recommended here consists in:

1. reacting 1 mol of 1-(4-aminophenyl)-2-dimethylaminopropanone with at least 2 mol of N-chlorosuccinimide, at a temperature of between 5° and 20° C., for at least 4 h, to give the compound of formula I in which R=H; and 2. if necessary, subjecting the said compound of formula I in which R=H to an acetylation reaction to give the compound of formula I in which R=CH$_3$CO.

Stage 1, is carried out with an excess of N-chlorosuccinimide relative to the stoichiometric conditions; the reaction is advantageously carried out at 10° C. when chlorosuccinimide is introduced in portions into a solution of 1-(4-aminophenyl)-2-dimethylaminopropanone in an appropriate solvent, and then continued at 15°-20° C. for 8-12 h.

In stage 2, 1 mol of 1-(4-amino-3,5-dichlorophenyl)-2-dimethylaminopropanone is treated at room temperature (15°-20° C.) with at least 3 mol of acetyl chloride in acetic acid for 8-12 h.

The compounds according to the invention have beneficial therapeutic properties. They act in particular as antidepressants for the CNS and possess sedative effects which are unexpected in view of the psychostimulant and/or arousing effects of the homologous compounds CP-1 and CP-2.

Furthermore, 1-(4-acetylamino-3,5-dichlorophenyl)-2-dimethylaminopropanone and non-toxic addition salts thereof are particularly valuable for their immunological properties in the sense that they act as immunostimulants, especially towards cellular immunity and towards humoral immunity.

According to the invention, a therapeutic composition is recommended which contains, in association with a physiologically acceptable excipient, at least one derivative selected from the compounds of formula I and non-toxic addition salts thereof.

Of course, in a composition of this type, the active principle, namely the compound of formula I or one of the non-toxic salts thereof, is present in a pharmaceutically effective amount.

According to the invention, the use of a substance selected from the group consisting of: (i) 1-(4-acetylamino-3,5-dichlorophenyl)-2-dimethylaminopropanone, (ii) 1-(4-amino-3,5-dichlorophenyl)-2-dimethylaminopropanone and (iii) non-toxic addition salts thereof, is recommended for the preparation of an antidepressant for the CNS which is to be used in human therapy for the treatment of depressions and depressive states.

According to the invention, the use of a substance selected from the group consisting of 1-(4-acetylamino-3,5-dichlorophenyl)-2-dimethylaminopropanone and non-toxic addition salts thereof is also recommended for the preparation of an immunostimulant which is to be used in human therapy in the case where immunostimulation is required.

Further advantages and characteristics of the invention will be understood more clearly from the following description of Preparative Examples and results of pharmacological tests; these data as a whole do not in any way imply a limitation but are given by way of illustration.

PREPARATION I

Preparation of 1-(4-acetylamino-3,5-dichlorophenyl)-2-dimethylaminopropanone monohydrochloride Example 1; code no.: CRL 41 403

A mixture of 16 g (0.053 mol) of 1-(4-amino-3,5-dichlorophenyl)-2-dimethylaminopropanone hydrochloride (code no.: CRL 41 402) and 11.5 ml (0.160 mol) of acetyl chloride in 75 ml of acetic acid is stirred overnight. The reaction mixture is evaporated to dryness under reduced pressure and the evaporation residue is taken up with acetone. On filtration, 16.6 g (yield: 92.25%) of CRL 41 403 are collected in the form of a beige powder. M.p.=about 200° C. (with decomposition).

PREPARATION II

Preparation of 1-(4-amino-3,5-dichlorophenyl)-2-dimethylaminopropanone monohydrochloride Example 2; code no.: CRL 41 402

26.7 g (0.200 mol) of N-chlorosuccinimide are introduced in portions, over 1 hour, into a solution, kept at about 10° C., of 22.5 g (0.083 mol) of 1-(4-aminophenyl)-2-dimethylaminopropanone dihydrochloride (code no.: CRL 41 233; reference here: CP-1) in 100 ml of water, and the reaction medium is then left overnight at room temperature (15°-20° C.). The precipitate formed is collected by filtration and the said precipitate is washed with hot acetone to give 17 g (yield: 68.85%) of CRL 41 402 in the form of a beige powder with a solubility in water of 50 g/l. M.p.$_{inst.}$>260° C.

The results of the toxicological, neuropsychopharmacological and immunological tests undertaken with the compounds according to the invention have been summarized below.

A. Tests Relating to CRL 41 403 (Product of Example 1) -Neuropsychopharmacological Study In the neuropsychopharmacological study which follows, a solution of CRL 41 403 in distilled water (solution of pH 5.5) was administered intraperitoneally in a volume of 20 ml/kg to male mice and in a volume of 5 ml/kg to male rats.

I. TOXICITY

In male mice, the LD$_0$ (maximum non-lethal dose) by intraperitoneal administration is greater than 128 mg/kg and the LD$_{60}$ (lethal dose for 60% of the animals treated) is of the order of about 256 mg/kg (at this dose, the mice die within 24 hours of I.P. administration of the CRL 41 403). The LD$_{100}$ (minimum lethal dose for all the animals treated) is less than 512 mg/kg (at this dose, the mice die within 8-10 minutes of administration of the CRL 41 403).

II. OVERALL BEHAVIOR AND REACTIVITIES

Groups of three animals are observed before and then 0.25 h, 0.50 h, 1 h, 2 h, 3 h and 24 h after the administration of CRL 41 403. The following observations are made:

1. in mice at doses of 1 mg/kg, 4 mg/kg and 16 mg/kg:

a behavior and reactivities substantially comparable to those of the control group;
at a dose of 64 mg/kg:
a decrease in the breathing rate with mydriasis for 2 hours;
at a dose of 128 mg/kg:
sedation,
a very moderate hypothermic effect, and
a decrease in the breathing rate; and 2. in rats
at doses of 0.25 mg/kg, 2 mg/kg and 8 mg/kg:
a behavior, reactivities and a variation in the rectal temperature and the pupil diameter substantially comparable to those of the control group;
at a dose of 32 mg/kg:
mydriasis for 1 h.

III. INTERACTION WITH APOMORPHINE

1. In mice

Groups of 6 mice receive the test product, by I.P. administration, 0.5 h before the subcutaneous injection of 1 or 16 mg/kg of apomorphine. It is observed that, as from a dose of 1 mg/kg and especially at a dose of 64 mg/kg, CRL 41 403 opposes the hypothermia induced by apomorphine without modifying the righting behavior and the stereotypies.

It should be pointed out that, at the highest dose used (64 mg/kg), the very moderate hypothermic effect of CRL 41 403 is apparent before the injection of apomorphine.

2. In rats

The test product is administered to groups of 6 rats 0.5 h before the subcutaneous injection of 0.5 mg/kg of apomorphine. It is observed that, as from a dose of 0.5 mg/kg, CRL 41 403 does not modify the stereotypies induced by apomorphine.

IV. INTERACTION WITH AMPHETAMINE

Amphetamine (2 mg/kg) is injected intraperitoneally into groups of 6 rats 30 minutes after the administration of the test product. It is found that, at doses of 1 mg/kg to 64 mg/kg, CRL 41 403 does not modify the stereotypies induced by amphetamine.

V. INTERACTION WITH RESERPINE

Four hours after the intraperitoneal injection of 2.5 mg/kg of reserpine, groups of 6 mice receive the test product.

It is noted that, as from a dose of 1 mg/kg and especially at doses of 16 mg/kg and 64 mg/kg, CRL 41 403 opposes the hypothermia induced by reserpine [at lower doses (1 and 4 mg/kg), the antihypothermic effect is transient and is only apparent one hour after the administration of CRL 41 403]. It is furthermore observed that, at a dose of 16 mg/kg and especially at a dose of 64 mg/kg, CRL 41 403 decreases the ptosis induced by reserpine.

VI. INTERACTION WITH OXOTREMORINE

The product to be studied is administered to groups of 6 mice 0.5 h before the intraperitoneal injection of 0.5 mg/kg of oxotremorine.

1. Action on the temperature

As from a dose of 4 mg/kg and especially at a dose of 64 mg/kg, CRL 41 403 opposes the hypothermia induced by oxotremorine. It should be noted that, at the highest dose used (64 mg/kg), the hypothermic effect of CRL 41 403 is apparent before the administration of oxotremorine.

2. Action on the trembling

It is found that, at the highest dose used (64 mg/kg), CRL 41 403 causes a moderate decrease in the intensity of the trembling induced by oxotremorine.

3. Action on the peripheral cholinergic symptoms

It is observed that CRL 41 403 causes practically no modification of the signs of peripheral cholinergic stimulation due to oxotremorine.

VII. ACTION ON THE FOUR PLATE TEST, TRACTION AND ELECTRIC SHOCK

The test is performed on groups of 10 mice 30 minutes after the administration of the product to be studied.

It is found that CRL 41 403 causes practically no modification of the number of punished passes, does not cause major motor incapacity and does not modify the convulsant and lethal effects of electric shock.

VIII. ACTION ON THE SPONTANEOUS MOTILITY 0.5 h after they have received the product to be studied, the mice (12 per dose, 24 control animals) are placed in an actimeter, where their motility is recorded for 30 minutes.

It is found that, at the two highest doses used (16 and 64 mg/kg), CRL 41 403 causes a moderate decrease in the spontaneous motor activity of the mice.

IX. ACTION ON THE INTERGROUP AGGRESSIVENESS

After they have stayed for 3 weeks in the two halves of a cage divided by an opaque partition, groups of 3 mice receive the product to be studied. Half an hour later, the two groups from the same cage are brought together by removal of the partition and the number of fights which occur in 10 minutes is noted.

It is found that, at a dose of 16 mg/kg and especially at a dose of 64 mg/kg, CRL 41 403 distinctly decreases the number of fights.

X. ACTION TOWARDS SOME FORMS OF BEHAVIOR PERTURBED BY VARIOUS AGENTS

1. Motility reduced by habituation to the enclosure

After they have stayed in the actimeters for 18 hours, the mice (6 per dose, 12 control animals) receive the test product. They are immediately returned to their respective enclosures and, half an hour later, their motility is recorded for 30 minutes.

It is observed that CRL 41 403 does not cause a resumption in the motor activity of mice accustomed to their enclosure.

2. Motility reduced by hypoxic aggression

Half an hour after they have received the test product, the mice (10 per dose, 20 control animals) are subjected to acute hypobaric anoxia [pressure reduction of 600 mm Hg (i.e. about $8 \times 10^4$ Pa) in 90 seconds, followed by release of vacuum in 45 seconds] and are then placed in an actimeter, where their motility is recorded for 10 minutes.

It is observed that, at a dose of 64 mg/kg, CRL 41 403 causes a distinct improvement in the motor recovery of mice whose motility has been depressed following a brief period in a reduced-pressure enclosure.

3. Asphyxiant anoxia

Groups of 10 mice receive the test product half an hour before the intraperitoneal administration of 32 mg/kg of gallamine triiodoethylate (reference curarizing agent).

It is observed that CRL 41 403 causes practically no modification of the time taken for convulsions and death to occur following asphyxiant anoxia caused by a curarizing agent.

XI. INTERACTION WITH BARBITAL

Half an hour after the administration of the product to be studied, groups of 10 mice receive an intraperitoneal injection of barbital (220 mg/kg).

It is noted that, at the highest dose used (64 mg/kg), CRL 41 403 distinctly decreases the duration of the sleep induced by barbital.

XII. ACTION ON THE "BEHAVIORAL DESPAIR"

Half an hour after they have received the test product, groups of 6 mice are placed in a beaker filled with water to a height of 6 cm. The total period of immobility between the second and sixth minutes following immersion is noted.

It is observed that, at the highest dose studied (64 mg/kg), CRL 41 403 decreases the period of immobility of mice which have been forcibly immersed.

XIII. CONCLUSIONS

The above neuropsychopharmacological tests as a whole show that CRL 41 403 has:

antidepressant effects illustrated by antagonism of the hypothermia induced by apomorphine, reserpine or oxotremorine, and by the decrease, at high doses, in the period of immobility due to "despair"; and sedative effects appearing only at high doses and illustrated by a moderate decrease in the spontaneous motor activity of mice, a decrease in the intergroup aggressiveness of mice and hypothermia in mice.

These sedative effects makes it possible to differentiate between CRL 41 403 and its above-mentioned homologs CP-1 and CP-2, which exert arousing and stimulant effects at high doses.

In addition to these sedative effects, CRL 41 403 has arousing and antihypoxic activities at certain points in its neuropsychopharmacological profile. The arousing activity is illustrated by a decrease in the duration of the sleep induced by barbital. The antihypoxic activity (which is not due to a stimulant and/or anticonvulsant effect) is illustrated by a distinct improvement in the motor recovery after acute hypobaric hypoxia.

These arousing and antihypoxic activities at certain points are paradoxically surprising since, at the highest dose used (64 mg/kg), CRL 41 403 has, as illustrated above, sedative effects which are manifestly opposite to the said arousing and antihypoxic activities.

Complementary Tests

Complementary tests were undertaken by gastric administration to rats in order to assess any toxicity associated with this mode of administration.

CRL 41 403, in solution in distilled water for concentrations less than or equal to 6.4 g/l, or in suspension in an aqueous solution of gum arabic for concentrations greater than or equal to 12.4 g/l, was administered to male rats in a volume of 5 ml/kg by means of an appropriate gastric tube.

Groups of 3 rats are observed before and then 0.25 h, 0.50 h, 1 h, 2 h, 3 h and 24 h after the gastric administration of CRL 41 403. The following observations are made:

at doses of 2 mg/kg, 8 mg/kg, 32 mg/kg and 128 mg/kg:
a behavior, reactivities and a variation in the rectal temperature and the pupil diameter substantially comparable to those of the control group;

at doses of 256 mg/kg and 512 mg/kg:
no particular symptom;

at a dose of 1024 mg/kg:
sedation,
an increase in the salivation,
a decrease in the breathing rate, and
no mortality.

It is therefore observed, under the present experimental conditions, that CRL 41 403, administered gastrically to rats, is not toxic and only shows distinct modifications of the behavior at the highest dose used. The increase in salivation seems to be related to a component of alpha-adrenergic stimulation already observed after I.P. administration (mydriasis in mice, decrease in the ptosis induced by reserpine).

Immunological Study

The properties of CRL 41 403 as an immunomodulator were studied in accordance with several protocols by comparison with CRL 41 402 (product of Example 2), CRL 41 233 described in European patent document No. B-0 174 242 (and denoted by CP-1 here) and CRL 41 232 described in European patent document No. B-0 138 714 (and denoted by CP-2 here).

Specifically, the tests used were, on the one hand, the so-called test for cells forming lysis areas, described by A. J. CUNNINGHAM et al. ("Further improvements in the plaque technique for detecting simple antibody forming cells"), Immunology 14, pages 599–601 (1968), and on the other hand the so-called test for the intensity of the delayed hypersensitivity to the red blood corpuscles of sheep, described by T. E. MILLER et al. ("Immunopotentiation with BCG II modulation of the response to sheep blood cells"), Journal of the National Cancer Institute 51 (no. 5), pages 1669–1676 (1973).

1. The test for cells forming lysis areas (or PFC IgM) explores the humoral immunity. Four days after immunization with a T-dependent antigen (in this case red blood corpuscles of sheep), the spleen cells expressing a direct IgM antibody response are counted. The mice used for this purpose are conventional female $OF_1$ mice devoid of specific pathogenic organisms, weighing from 20 to 30 g and divided up into a control group of 14 animals and groups each containing 7 animals per dose and per product to be studied, administered orally on the same day as the antigen. An activity index I is calculated for each dose of product according to the following equation:

$$I = \frac{\text{mean of lyses per spleen for the treated mice}}{\text{mean of lyses per spleen for the control mice}}$$

This test is performed at least twice for each dose of test product (0.001, 0.01, 0.1, 10 and 100 mg/kg) and a statistical study is undertaken using the Student t test after variance analysis on the number of lyses per spleen.

The activity index is found to increase at all doses for CRL 41 403, reaching the value I=2 at a dose of 100 mg/kg P.O., whereas the other three products, Ex. 2, CP-1 and CP-2, do not modify the said activity index.

2. The test for the intensity of the delayed hypersensitivity to the red blood corpuscles of sheep is a technique for exploring the cellular immunity. The compound to be studied is administered either orally, if it is insoluble, or (as is the case here) subcutaneously into the pad of the paw, if it is soluble in water, the said compound being administered three days before immunization (by the subcutaneous administration of red blood corpuscles of sheep into the pad) to conventional female $OF_1$ mice divided up into a control group of 10 animals and groups each containing 5 animals per dose and per product to be studied. The results obtained are expressed as the percentage increase in the thickness of the pad.

This test is performed at least twice for each dose of test product (0.001, 0.01, 0.1, 10 and 100 mg/kg) and a statistical study is undertaken as indicated above.

It is found that CRL 41 403 is the only product tested which gives a positive delayed hypersensitivity reaction. At a dose of 100 mg/kg S.C., CRL 41 403 induces a variation in the percentage increase in the thickness of the pad of 16.40±4.06, whereas the control animals show a percentage variation of 8.28±1.14.

All these results, especially the results collated in Table II below, demonstrate that CRL 41 403 (i) is an immunomodulator, as distinct from the other three products, and (ii) has a more precise action as an immunostimulant.

TABLE II

IMMUNOLOGICAL STUDY
COMPARATIVE TESTS

| Product | Code no. | Dose (a) | I (b) | DHS (c) |
|---|---|---|---|---|
| Ex. 1 | CRL 41 403 | 100 | 2.00* | 16.40* |
| Ex. 2 | CRL 41 402 | 10 | 1.09 | 8.26 |
| CP-1 | CRL 41 233 | 100 | 0.98 | 8.29 |
| CP-2 | CRL 41 232 | 100 | 1.01 | 8.27 |
| control animals | — | — | 1 | 8.28 |

Notes
(a) dose expressed in mg/kg, the mode of administration being oral for measurement of the activity index I and subcutaneous for measurement of the delayed hypersensitivity DHS;
(b) activity index according to the so-called test for cells forming lysis areas:
$$I = \frac{\text{mean of lyses per spleen for the treated mice}}{\text{mean of lyses per spleen for the control mice}}$$
(c) intensity of the delayed hypersensitivity to the red blood corpuscles of sheep, expressed as the percentage increase in the thickness of the pad;
*result statistically significant relative to the control animals.

B. Tests Relating to CRL 41 402 (Product of Example 2)

The neuropsychopharmacological study of CRL 41 402 was undertaken according to the procedures described above for CRL 41 403, the CRL 41 402 to be studied being administered intraperitoneally in solution in distilled water for concentrations less than 25 g/l, or in suspension in an aqueous solution of gum arabic for concentrations greater than or equal to 25 g/l, in a volume of 20 ml/kg to male mice and in a volume of 5 ml/kg to male rats.

The pH of the composition administered varies moderately as a function of the concentration of CRL 41 402: it drops from 6.0 for a concentration of 125 g/l to 5.5 for concentrations less than or equal to 6.4 g/l.

I. TOXICITY

The $LD_0$ of CRL 41 402 is greater than 32 mg/kg. The $LD_{30}$ of CRL 41 402 by intraperitoneal administration is of the order of 64 mg/kg.

II. OVERALL BEHAVIOR AND REACTIVITIES 1. in mice
at doses of 0.25 mg/kg, 1 mg/kg and 4 mg/kg:
a behavior and reactivities substantially comparable to those of the control group;
at a dose of 16 mg/kg:
salivation appearing for about 0.5 h between half an hour and one hour after administration of the CRL 41 402,
sedation,
a decrease in the breathing rate, and
moderate hypothermia for 3 h (variation of −1.4° C. 1 h after administration of the CRL 41 402, whereas under the same operating conditions, the temperature variation for the control animals is −0.9° C.);
at a dose of 32 mg/kg:
sedation,
a decrease in the breathing rate, and
salivation; and 2. in rats
at doses of 0.125 mg/kg, 0.5 mg/kg and 2 mg/kg:
a behavior, reactivities and a variation in the rectal temperature and the pupil diameter substantially comparable to those of the control group;
at a dose of 8 mg/kg:
moderate mydriasis for 2 h.

III. INTERACTION WITH APOMORPHINE

In mice, at doses of 0.25 mg/kg, 1 mg/kg and especially 4 mg/kg and 16 mg/kg, CRL 41 402 opposes the hypothermia induced by apomorphine but does not modify the righting behavior.

In rats, it is found that CRL 41 402 does not modify the stereotypies induced by apomorphine.

IV. INTERACTION WITH AMPHETAMINE

It is observed that CRL 41 402 causes practically no modification of the stereotypies caused by amphetamine.

V. INTERACTION WITH RESERPINE

At doses of 1 mg/kg, 4 mg/kg and 16 mg/kg, CRL 41 402 distinctly antagonizes the hypothermia induced by reserpine.

VI. INTERACTION WITH OXOTREMORINE

At doses of 4 and 16 mg/kg, CRL 41 402 opposes the hypothermic action of oxotremorine.

CRL 41 402 does not modify the trembling caused by oxotremorine.

Finally, CRL 41 402 seems not to cause a distinct modification of the signs of peripheral cholinergic stimulation due to oxotremorine.

VII. ACTION ON THE FOUR PLATE TEST, TRACTION AND ELECTRIC SHOCK

It is observed that CRL 41 402 does not modify the number of punished passes, does not cause major motor incapacity and does not modify the convulsant and lethal effects of electric shock.

VIII. ACTION ON THE SPONTANEOUS MOTILITY

It is found that, at the two highest doses used (4 and 16 mg/kg), CRL 41 402 causes a moderate decrease in the spontaneous motility of mice.

IX. ACTION ON THE INTERGROUP AGGRESSIVENESS

It is observed that, as from a dose of 1 mg/kg, CRL 41 402 distinctly decreases the number of fights.

X. ACTION TOWARDS SOME FORMS OF BEHAVIOR PERTURBED BY VARIOUS AGENTS

1. Motility reduced by habituation to the enclosure

It is found that CRL 41 402 does not cause a distinct resumption in the motor activity of mice accustomed to their enclosure.

2. Motility reduced by hypoxic aggression

At a dose of 4 mg/kg and especially at a dose of 16 mg/kg, CRL 41 402 causes a distinct improvement in the motor recovery of mice whose motility has been depressed following a brief period in a reduced-pressure enclosure.

3. Asphyxiant anoxia

CRL 41 402 causes practically no modification of the time taken for convulsions and death to occur following asphyxiant anoxia caused by a curarizing agent.

XI. INTERACTION WITH BARBITAL

It is found that CRL 41 402 does not modify the duration of the sleep induced by barbital.

XII. ACTION ON THE "BEHAVIORAL DESPAIR"

It is found that, at the highest dose used (16 mg/kg), CRL 41 402 distinctly decreases the period of immobility of mice which have been forcibly immersed.

XIII. CONCLUSIONS

The neuropsychopharmacological tests as a whole demonstrate that CRL 41 402 has:

antidepressant effects illustrated by antagonism of the hypothermia induced by apomorphine, oxotremorine or reserpine, and by the decrease in the immobility due to "despair"; and moderate sedative effects illustrated by a (slight) decrease in the motor activity, associated on the one hand with a decrease in the aggressiveness and on the other hand with modest hypothermia.

In clinical trials, good results were obtained by administering CRL 41 403 to adults, on the one hand as an antidepressant and on the other hand as an immunostimulant. In particular, CRL 41 403 proved to be an excellent antidepressant at a daily dose of 15 mg (divided up into three individual doses of 5 mg), especially in burn victims suffering from depression.

What is claimed is:

1. A 1-(4-aminophenyl)-2-dimethylaminopropanone derivative which is selected from the group consisting of:

(a) the compound having the general formula

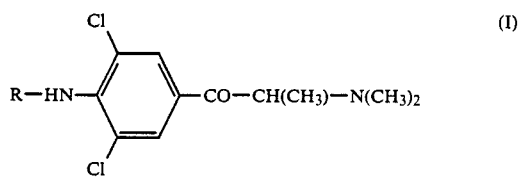

in which R is CH$_3$CO, and (b) addition salts thereof.

2. A therapeutic composition which contains, in association with a physiologically acceptable excipient, at least one compound selected from the compound of formula I according to claim 1 and non-toxic addition salts thereof.

3. A method of treatment against depression which comprises administering to a patient in need of such a treatment an antidepressive effective amount of an antidepressant and sedative substance selected from the group consisting of (a) the compounds having the general formula

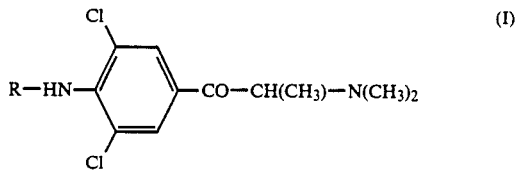

in which R is H or CH$_3$CO, and (b) non-toxic addition salts thereof.

* * * * *